(12) United States Patent
Wieringa

(10) Patent No.: US 6,775,565 B1
(45) Date of Patent: Aug. 10, 2004

(54) IMAGING APPARATUS FOR DISPLAYING CONCENTRATION RATIOS

(75) Inventor: Fokko Pieter Wieringa, Duiven (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 251 days.

(21) Appl. No.: 10/070,095

(22) PCT Filed: Aug. 30, 2000

(86) PCT No.: PCT/NL00/00604

§ 371 (c)(1),
(2), (4) Date: Apr. 18, 2002

(87) PCT Pub. No.: WO01/15597

PCT Pub. Date: Mar. 8, 2001

(30) Foreign Application Priority Data

Aug. 31, 1999 (NL) .............................................. 1012943

(51) Int. Cl.[7] .................................................. A61B 5/00
(52) U.S. Cl. ........................ 600/322; 600/342; 600/476
(58) Field of Search ................................. 600/310–344, 600/473–480

(56) References Cited

U.S. PATENT DOCUMENTS 5,408,998 A    4/1995   Mersch

FOREIGN PATENT DOCUMENTS

| EP | 0 488 565 A1 | 6/1992 |
| EP | 0 793 942 A2 | 9/1997 |
| WO | WO 98/44839 | 10/1998 |
| WO | WO 99/40840 | 8/1999 |

*Primary Examiner*—John P. Lacyk
(74) *Attorney, Agent, or Firm*—Leydig, Voit & Mayer Ltd.

(57) ABSTRACT

Imaging apparatus for representing an image of concentration ratios between a first and a second substance in a region of interest of an object, with different measuring values being represented with different colors and/or gray shades. The apparatus comprises a light source capable of irradiating the object with light, which light comprises at least three wavelengths $\lambda_1$, $\lambda_2$ and $\lambda_3$, $\lambda_3$ being an isobestic wavelength, $\lambda_1$ being a wavelength at which the first substance has a lower absorption than the second substance, and $\lambda_2$ being a wavelength at which the first substance has a higher absorption than the second substance. The apparatus further comprises detection means comprising a matrix of pixel detectors, for representing a virtually instantaneous image of the region of interest.

4 Claims, 2 Drawing Sheets

IMAGING APPARATUS FOR DISPLAYING CONCENTRATION RATIOS

This invention relates to an imaging apparatus for representing an image of concentration ratios between hemoglobin and oxyhemoglobin in blood, with different measuring values being represented with different colors and/or gray shades, comprising a light source capable of irradiating the object with light, which light comprises at least three wavelengths λ1, λ2 and λ3, wherein λ1 is in the wavelength range of 600 to 700 nm, with a preference for 660 nm, λ2 is in the wavelength range of 900 to 1000 nm, with a preference for 940 nm, and λ3 is in the wavelength range of 790 to 830 nm, with a preference for 810 nm; detection means for at least detecting the intensity of light emitted by the object at the respective wavelengths λ1, λ2 and λ3, resulting in detection signals S1, S2 and S3 ; a processing unit for calculating an optical image of the pattern of concentration ratios, from the respective signals S1, S2 and S3; display means for displaying the calculated optical image Such an apparatus as described in the preamble is known from U.S. Pat. No. 5,318,022. In this patent specification, it is described how with a narrow light beam consisting of three wavelengths a human eye is scanned, malting use of the different absorption behavior of blood at different wavelengths. This is caused by the different absorption characteristics of oxyhemoglobin ($HbO_2$) and deoxyhemoglobin (Hb). The wavelengths are selected such that light of a first wavelength $\lambda_1$ sustains a relatively low absorption in oxygen-rich blood, while light of a second wavelength $\lambda_2$ is absorbed relatively strongly in oxygen-rich blood, both in relation to an absorption in oxygen-poor blood. The so-called isobestic wavelength $\lambda_3$ is the wavelength at which no difference in absorption occurs with respect to oxygen-poor blood. This wavelength $\lambda_3$ lies between the first and second wavelengths $\lambda_1$ and $\lambda_2$ and serves as reference.

Of interest, in practice, is the concentration ratio of those two substances, represented formulaically by $$\frac{HbO_2}{Hb + HbO_2} \times 100\%.$$

It is clear that the apparatus according to the known technique is not suitable for making optical images with a high resolution, both in the time domain and in the place domain. An intrinsic limit on this resolution is imposed in that the images are built up by sequentially scanning a grid-shaped pattern with a narrow beam, from which an image is derived through synchronization. Clearly, such an apparatus can only yield images of limited grade. In particular, the apparatus is not suitable for producing a virtually instantaneous image of a region of interest of an object, which can be analyzed with sufficient resolution in time.

The object of the invention is to enable a reliable detection of the oxygen content in blood, which can be performed virtually continuously in time. To that end, the invention provides an imaging apparatus as described in the preamble, wherein the apparatus is further characterized according to characterizing part of claim 1. This renders sequential scanning of a grid pattern superfluous, so that the feasible image frequency increases by a factor equal to the square of the desired number of pixels/inch. Thus, virtually instantaneous measuring results over a whole region of interest can be obtained. The combination of an image of visible light with the image of the oxygen concentration levels and/or the vascular system (called SpO2 image for short) provides advantages in the application of the invention in probe examination, the probe then being provided with the apparatus according to the invention. By reading out the images of visible light, steering can be roughly controlled, while through the measuring signals in situ au accurate picture of the vascular system and/or the oxygen concentrations therein can be obtained. The image of visible light and the pattern of concentrations or concentration changes can be projected in a single overlapping image, which improves orientation in the body in manipulating the probe.

In a preferred embodiment, the light signals $S_1$, $S_2$ and $S_3$ have a characteristic modulation. What is thus achieved is that the apparatus can be made insensitive to non-modulated signals, such as ambient light. Also, if the sensors in the apparatus have a sensitivity to different wavelength bands, the contributions of the different wavelengths to the output signal of the apparatus can be determined by demodulation of the signal. Modulating the light signal, finally, affords the possibility of raising the light intensity to a maximum without this leading to distortion. The applications hereof will be further elucidated in the description of the drawings.

In a further preferred embodiment, the imaging apparatus is suitable for determining measurements consecutive in time. The apparatus may further comprise means for analyzing the measuring values. Relevant parameters can be determined and analyzed, such as the time-average value and deviation, minimum and maximum, as well as, given an assumed cyclic change of the concentration ratio, the spectral features of the waveform.

In an application of the invention as a detector for determining the ratio of hemoglobin and oxyhemoglobin in blood, with the first and second substance being hemoglobin and oxyhemoglobin, respectively, the signal sources are so arranged that the first wavelength $\lambda_1$ is in the wavelength range of 600 to 700 nm, with a preference for 660 nm, the second wavelength $\lambda_2$ is in the wavelength range of 900 to 1000 nm, with a preference for 940 nm, and the third wavelength $\lambda_3$ is in the wavelength range of 790 to 830 nm, with a preference for 810 nm.

Preferably, the apparatus further comprises means for analyzing the measured values numerically. Such means can be image analysis means. They may also be means that represent the value of the reference signal $S_3$, thus yielding an image of the light absorption that is independent of the oxygen level. This reflects the actual vascular volume, which enables plethysmographic measurements to be performed. The means can comprise the analysis means mentioned earlier, as well as the possibility of determining region averages and the time development of such parameters. The means may further comprise indicating means for defining such a region of interest, such as a light pen, tracker ball or mouse indication. Also, the analysis means may comprise the possibility of comparing the measuring values with reference values, or with the values measured in corresponding parts in the left-side or right-side parts of the body.

The measuring signals $S_1$, $S_2$ and $S_3$ can be distinguished from the visible light by modulation technique.

The invention further relates to an image observing apparatus, such as a camera or endoscope with an imaging apparatus as described above.

In the following, the invention will be further elucidated with reference to the drawings, wherein FIG. 1 is a graphic representation of the spectral absorption capacity of deoxyhemoglobin (Hb) and oxyhemoglobin ($HbO_2$);

Figure 1:
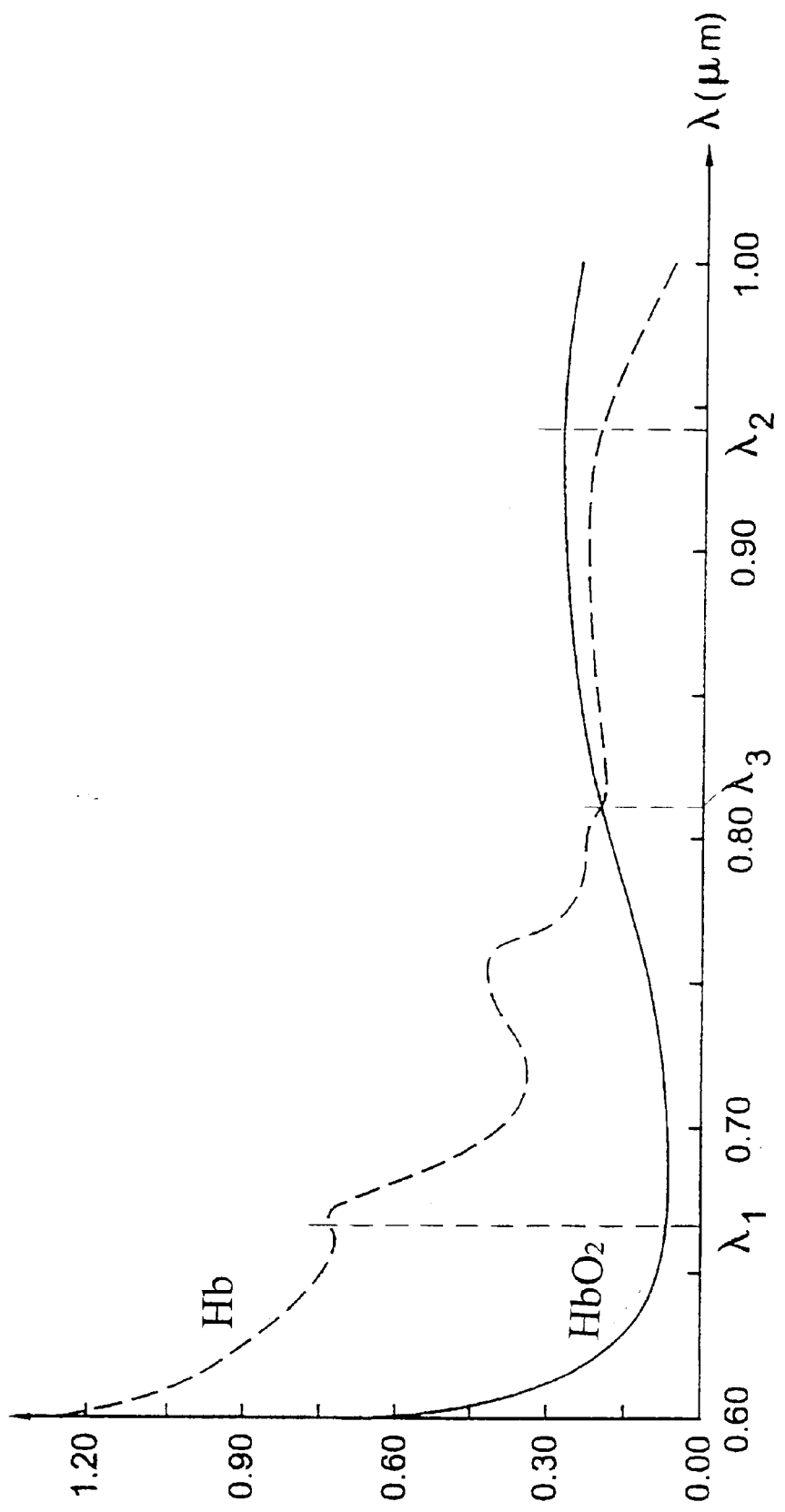

Referring to FIG. 1, the broken line reflects the spectral absorption capacity of deoxyhemoglobin (Hb), while the full line reflects the spectral absorption capacity of oxyhemoglobin ($HbO_2$ in $10^{-6} cm^2$/equivalent. In the figure, it can be seen that the absorption capacity of Hb as well as of $HbO_2$ is virtually constant at 660 to 670 nm. This range relates to the first wavelength $\lambda_1$ mentioned in the preamble, at which the absorption coefficient of $HbO_2$ is much lower than that of Hb. This accounts for the brightly red color of oxygen-rich blood. At 810 nm the absorption capacity of Hb and $HbO_2$ is equally large (isobestic point). This wavelength relates to the third wavelength $\lambda_3$ mentioned in the preamble. Above this wavelength, $HbO_2$ absorbs more strongly, in particular in the range around 940 nm, which wavelength corresponds to the second wavelength $\lambda_2$ mentioned in the preamble. Through a comparative measurement at a wavelength above 810 nm with a measurement at about 660 nm, the ratio of Hb and HbO2 can be determined.

Figure 2:
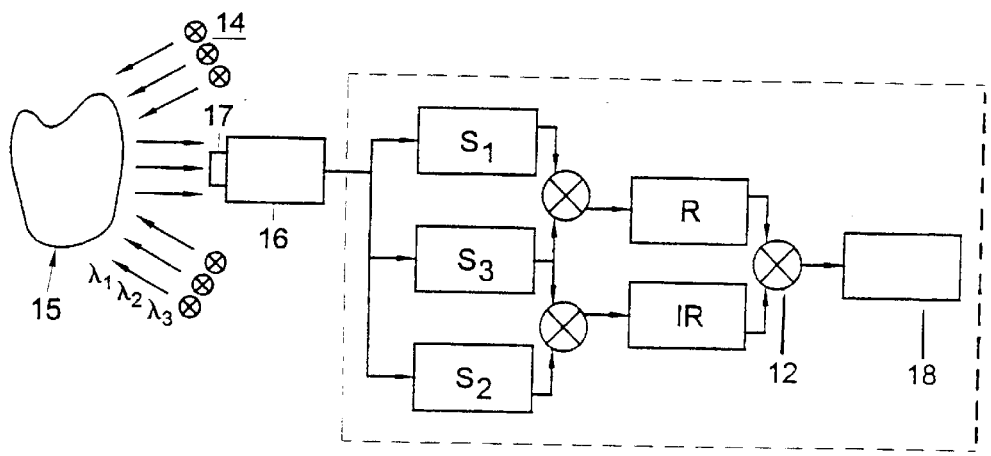
FIG. 2 is a of an imaging apparatus according to the invention.

FIG. 2 schematically represents a setup for a reflection measurement on an object 15, which consists of biological tissue. The object is illuminated by light source 14 with wavelengths $\lambda_1$, $\lambda_2$ and $\lambda_3$. The light source is arranged in a ring around a probe 16, so that a body part to be examined, which is disposed opposite the light passage 17, is uniformly exposed to light. The light that is reflected by the tissue is transmitted via glass fiber, optical fibers and/or lens systems to a camera, which has a sensitivity range in the above-mentioned wavelength ranges around $\lambda_1$, $\lambda_2$ and $\lambda_3$. The invention can be applied, for instance, by modifying commercially available CCD cameras or CMOS cameras by adapting the sensitivity range of the sensors by employing the filters as has been described hereinabove. In a preferred embodiment that utilizes a so-called 3 CCD camera, simultaneous measurements at the relevant wavelengths can be performed. It is also possible, however, to modify a simple black-and-white CCD camera, in which case, however, a (three times) lower sampling frequency needs to be used.

The signals $S_1$, $S_2$ and $S_3$ coming from the camera are combined into a normalized red image R, by subtraction of the signals $S_1$ and $S_3$, and into a normalized infrared image IR, by subtraction of the signals $S_2$ and $S_3$. The signals are subsequently applied to processing unit 12, which calculates the concentration ratio by comparing the signals $S_1$ and $S_2$ with respect to the signal $S_3$ by determining the ratio of the difference signal that is obtained by subtraction of the signals $S_1$ and $S_3$ and the difference signal that is obtained by subtraction of the signals $S_2$ and $S_3$.

The output values are graphically represented by means of a sliding color scale in a screen 18, where low output values, corresponding to a relatively low oxygen concentration, are indicated by a blue color, and high output values, corresponding to a relatively high oxygen concentration, are indicated by a red color. Further, the apparatus, given a sufficiently high sampling frequency, affords the possibility of representing the time-derived image, with high oxygen concentration fluctuations reflecting regions with an evidently high oxygen uptake. As such, the apparatus according to the invention provides the possibility of tracing tumors (in which an increased oxygen consumption occurs). The technique is further suitable for the in vivo analysis of oxygen concentration in a tissue, thus yielding possibilities for vascular diagnostics. Tissue can be inspected for blood saturation, thrombosis and burns. In a surgical application, the technique offers possibilities of visualizing infarcts.

Figure 3:
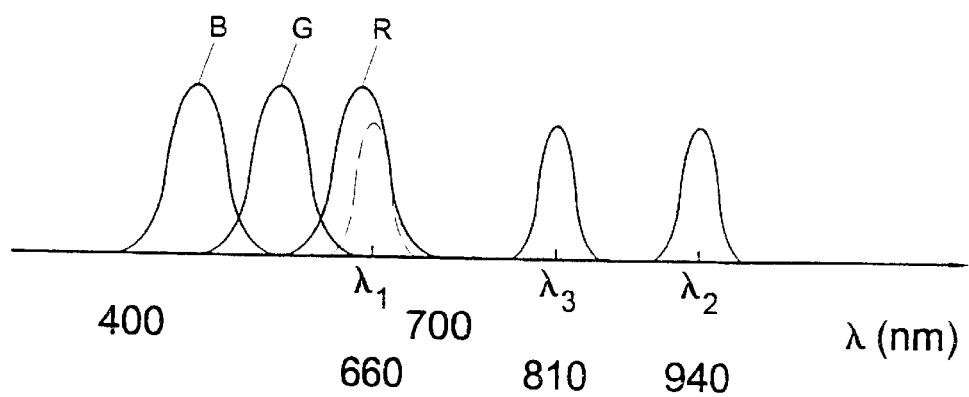
FIG. 3 is a representation of the spectral sensitivity of the light sensors arranged in the apparatus.

FIG. 3 represents the wavelength ranges in which the CCD camera is sensitive. A common color CCD camera has a triple band sensitivity, viz. one in the red (R) range, one in the green (G) range and one in the blue (B) range. With these color sensitivities, as is well known, light from the entire visible spectrum can be discerned. The camera is stabilized for white light, so that a normal visible image can be projected. In addition, with the camera, for the purpose of determining the oxygen concentration, a calibration can be performed, whereby the camera is aimed at one or more surfaces having an absorption spectrum of a known value. In the SpO2 mode, the visible light is cut off by an optical low pass filter, and the sensor is sensitive to the wavelength range of $\lambda_1$, $\lambda_2$ and $\lambda_3$, respectively. This is the case when the red light sensor (R) is also sensitive to the $\lambda_1$ (660 nm), the green light sensor (G) has a sensitivity to $\lambda_2$ (940 nm), and the blue light sensor (B) has a sensitivity to $\lambda_3$ (810 nm). Other combinations are also possible, but these combinations offer the best results in practice. The camera can be alternately brought into the normal and $SPO_2$ mode by emitting alternately visible light and (infra)red light or by arranging an ancillary filter, so that the camera is rendered sensitive to a different wavelength range. A different manner of simultaneous sampling can be employed, for instance by modulating the measuring signal, and emitting the visible light with a constant intensity. By frequency decomposition of the signal, the visible light can be separated by the measuring light.

The alternation between the visible image and the $SPO_2$ image can be set by the user, so that, given a sufficiently high sampling, both images are available simultaneously. These images can be projected in one screen or on two separate screens.

In a separate mode, through a different processing of the measuring signal $S_3$, the carbon monoxide content in blood can be determined. The signal is then not used as a reference signal. The signal is related to the oxygen concentration in blood as determined in the classic manner (i.e. determined once per pulse). Since HbCO (i.e., carbon monoxide bound to hemoglobin) has a deviant absorption at 810 nm, the content of HbCO can subsequently be determined. The apparatus can be arranged such that work is done in alternating mode.

With the apparatus, for all registered time-dependent parameters, given a sufficiently high sampling frequency during a cardiac cycle the course can be analyzed, e.g. by means of Fourier analysis. The apparatus provides the possibility of analyzing the measured values numerically, and to determine time-average values and deviation, minima and maxima, etc., as well as the time development of such parameters. This is understood to mean, though not exclusively so: the provision of brighter or more contrastive images, inter alia by (noise) filtering. Also, the value of the reference signal $S_3$ can be separately represented, so that an image is formed of the light absorption that is independent of the oxygen level. This reflects the actual vascular volume, so that plethysmographic measurements can be performed. The apparatus affords the possibility of determining time-average values and deviation, minima and maxima, as well as region averages and time development of such parameters. The apparatus can further comprise indicating means for defining a region of interest, such as a light pen, tracker ball or mouse indication. Also, measuring values can be compared with reference values, or with the values measured in corresponding parts in left-side or right-side parts of the body.

Although the exemplary embodiments described relate to an endoscope, the technique can also be used in other invasive or non-invasive image observing equipment, such as an otoscope, colposcope or (surgery) microscope. Further, the invention can be employed in combination with other measuring devices, such as, for instance, an ECG apparatus or a monitoring monitor. As a consequence, it is possible, for instance, to relate the parameters registered by the apparatus according to the invention to an ECG curve. The invention is therefore not limited to the exemplary embodiments described with reference to the drawing, but comprises all kinds of variations thereof, naturally insofar as they fall within the scope of protection of the following claims.

What is claimed is:

1. An imaging apparatus for representing an image of concentration ratios between hemoglobin and oxyhemoglobin in blood, with different measuring values being represented with different colors and/or gray shades, comprising
    a light source capable of irradiating the object with light, which light comprises at least three wavelengths $\lambda_1$, $\lambda_2$ and $\lambda_3$, wherein $\lambda_1$ is in the wavelength range of 600 to 700 nm, with a preference for 660 nm, $\lambda_2$ is in the wavelength range of 900 to 1000 nm, with a preference for 940 nm, and $\lambda_3$ is in the wavelength range of 790 to 830 nm, with a preference for 810 nm;
    detection means for at least detecting the intensity of light emitted by the object at the respective wavelengths $\lambda_1$, $\lambda_2$ and $\lambda_3$, resulting in detection signals $S_1$, $S_2$ and $S_3$;
    a processing unit for calculating an optical image of the pattern of concentration ratios, from the respective signals $S_1$, $S_2$ and $S_3$;
    display means for displaying the calculated optical image; characterized in that the detection means comprise:
    a 3CCD camera comprising three CCDs and three filters, wherein each filter is for receiving on one of said three CCDs one of said wavelengths $\lambda_1$, $\lambda_2$, $\lambda_3$, and one of red, green and blue optical ranges, the three CCDs of said camera generating three simultaneous signals $S_1$, $S_2$, $S_3$ respectively, to be processed in said processing unit, thereby representing a virtually instantaneous image of the region of interest, the apparatus further being arranged for forming an image of visible light from said red, green and blue optical ranges, wherein the pattern of concentration ratios is projected in one overlapping image with the visible image.

2. An imaging apparatus according to claim 1, characterized in that the light signals of wavelengths $\lambda_1$, $\lambda_2$ en $\lambda_3$ have a characteristic modulation.

3. An imaging apparatus according to claim 2, characterized in that the apparatus comprises, given an assumed change of the concentration ratio during a cardiac cycle, means for analyzing the time-dependent features thereof.

4. An imaging apparatus according to claim 3, characterized in that the apparatus comprises means for analyzing a Fourier spectrum of the concentration ratio.

* * * * *